United States Patent [19]
Bennett et al.

[11] 3,945,383
[45] Mar. 23, 1976

[54] UNIT DOSE AMPUL FOR JET INJECTOR

[75] Inventors: Russell B. Bennett, Worthington; William Millicovsky; Howard B. Pritz, both of Columbus, all of Ohio

[73] Assignee: SmithKline Corporation, Philadelphia, Pa.

[22] Filed: Aug. 8, 1974

[21] Appl. No.: 495,626

[52] U.S. Cl............................. 128/272; 128/173 H
[51] Int. Cl.².......................................... A61J 1/06
[58] Field of Search............ 128/272, 173 H, 218 D, 128/218 R, 221; 222/389, 541, 327; 206/365

[56] References Cited
UNITED STATES PATENTS

| 3,073,307 | 1/1963 | Stevens | 128/221 |
| 3,434,473 | 3/1969 | Smith | 206/365 |
| 3,557,784 | 1/1971 | Shields | 128/173 H |
| 3,625,208 | 12/1971 | Frost et al. | 128/173 H |
| 3,667,657 | 6/1972 | Arias | 128/218 R |
| 3,688,765 | 9/1972 | Gasaway | 128/173 H |

Primary Examiner—Robert W. Michell
Assistant Examiner—Lee S. Cohen
Attorney, Agent, or Firm—Smith, Harding, Earley & Follmer

[57] ABSTRACT

A unit dose ampul for a jet injector has a tube open at one end and an integral nozzle at the other end with a piston in the tube to seal the open end of the tube and to advance liquid in the tube through the nozzle. A sealing cap encompasses the nozzle and the forward end of the tube and is secured to the tube, the cap having a peripheral area of weakness adjacent the nozzle of the ampul whereby a portion of the cap can be broken off to expose the end of the nozzle. The cap has an interlocking portion for removably securing the cartridge to a jet injector.

3 Claims, 8 Drawing Figures

UNIT DOSE AMPUL FOR JET INJECTOR

BACKGROUND OF THE INVENTION

Jet injectors employing unit dose ampuls of glass are known to the art as seen from U.S. Pat. No. 3,688,765. The prior art ampuls are unsatisfactory for a number of reasons. They do not have adequate provisions for keeping the ampul sterile until immediately before the inoculation is to be carried out. They have no provision for preventing the inoculator from becoming contaminated by contact with the flesh of the patient which is wetted with the medicament being administered. In addition, the prior art ampuls are awkward to secure to the injector since they do not have any securing means attached thereto but rely on securing means on the injector which must be removed before the ampul is inserted in the injector.

SUMMARY OF THE INVENTION

A unit dose ampul for a jet injector has a tube open at one end and an integral nozzle at the other end with a piston in the tube to seal the open end of the tube and to advance liquid in the tube through the nozzle. A sealing cap encompasses the nozzle and the forward end of the tube and is secured to the tube, the cap having a peripheral area of weakness adjacent the nozzle of the ampul whereby portions of the cap can be broken off to expose the end of the nozzle. The cap has means for removably securing the cartridge to a jet injector.

PREFERRED EMBODIMENT

Figure 2:
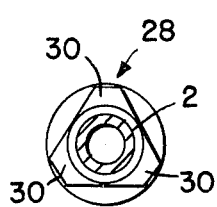
FIG. 2 is a section taken on the plane indicated by the line 2—2 in FIG. 1.
Figure 1:
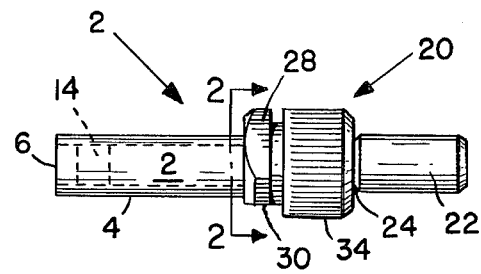
FIG. 1 is a side view of an ampul in accordance with the invention.

An ampul 2 in accordance with the invention has a tube 4 with an open end at 6 and a nozzle 8 at its other end. Nozzle 8 has an opening 10 of from about .003 to about .012 in diameter. Tube 4 may be formed from any suitable material such as metal or a plastic, for example, polycarbonate. A piston 14 acts to seal off open end 6 and prevent the contained liquid medicament 16 from escaping from tube 4, the nozzle opening 10 being sufficiently small so that the contained medicament 16 will pass therethrough only when subject to pressure. The ampul 2 as thus far described is well known in the art.

A sealing cap 20 overlies nozzle 8 and the forward end of tube 4 and is secured to tube 4 by an adhesive. If desired, a pressed fit can be used in lieu of an adhesive. Cap 20 has a tip 22 which is connected to the remainder of the cap by a frangible line of weakness indicated at 24 which is in a plane slightly to the rear of the outer end of nozzle 8. The line of weakness 24 permits the tip 22 to be broken off just before an injection is to be given in order to expose nozzle 8 for placement against the patient's skin. Integral with cap 20 is an interlocking portion 28 having three ears 30 (FIG. 2) which are adapted to interlock with a portion of an injector as is detailed later.

Between ears 30 and cap tip 22 is an enlarged knurled spool portion 34 which acts to keep the associated injector well spaced from the patient's skin to prevent contamination of the injector.

Cap 20 may be made of a wide variety of materials but preferably is made of a plastic such as, for example, polycarbonate ("LEXAN" sold by General Electric and "MERLON" sold by Mobay Chemical Co.), an acrylic plastic such as polymethyl methacrylate, polystyrene, acetal, polypropylene, or rigid polyvinyl chloride.

Figure 3:
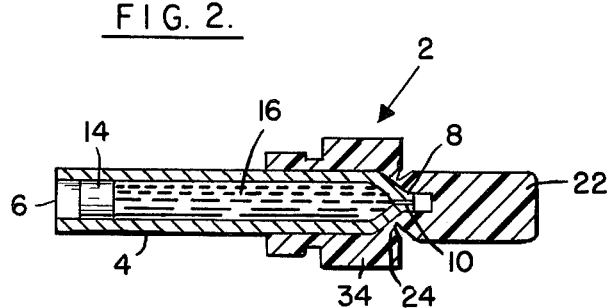
FIG. 3 is a vertical section through the ampul of FIG. 1.
Figure 4:
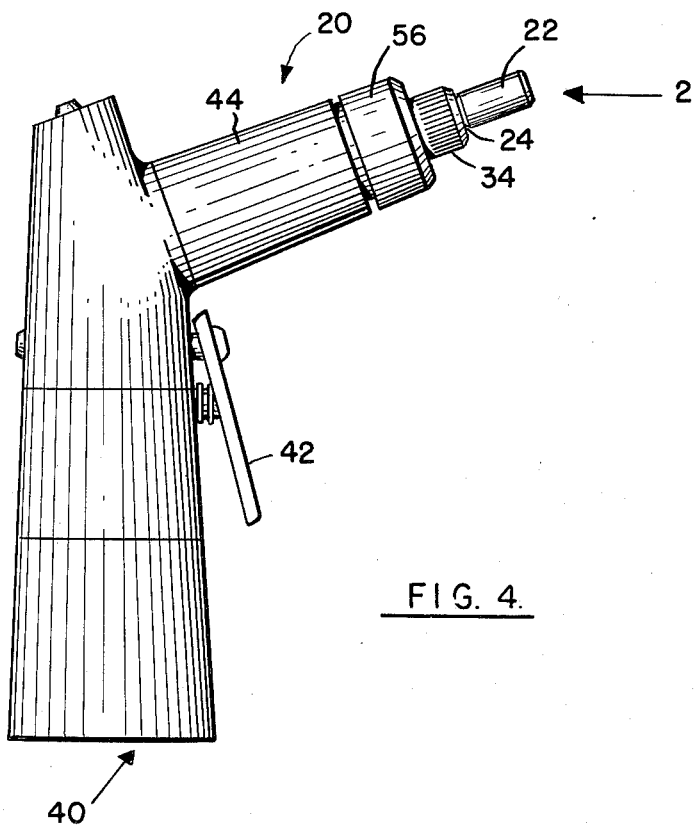
FIG. 4 is a side elevation of the ampul of FIG. 1 in a jet injector.
Figure 5:
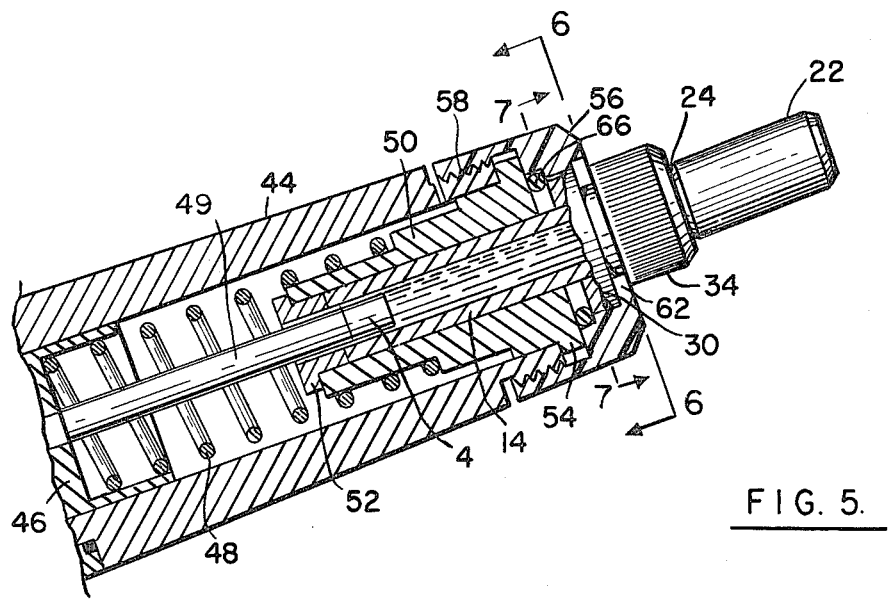
FIG. 5 is a vertical section, partially broken away, through the injector of FIG. 4.

The ampul 2 can be employed with any type of spring or gas actuated unit dose jet injector. By way of illustration, gas actuated injector 40 shown in FIG. 4 has an operating lever 42 and, as seen in FIG. 3, has secured thereto an ampul 2 in accordance with the invention. As best seen in FIG. 5, injector 40 has a cylinder 44 in which is mounted a piston 46 which is advanced by a gas admitted by structure not shown and biased in the retracted position shown by a compression coil spring 48. Piston 46 is connected to a rod 49 which enters tube 4 and abuts against plunger 14.

Figure 6:
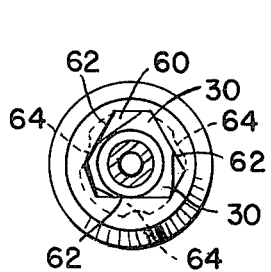
FIG. 6 is a section taken on the plane indicated by the line 6—6 in FIG. 5.
Figure 7:
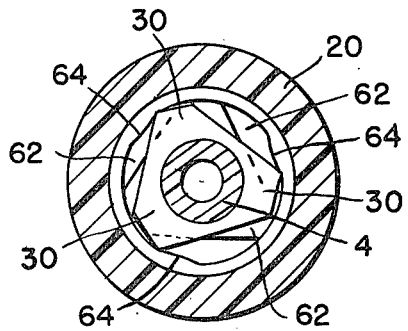
FIG. 7 is a section taken on the plane indicated by the line 7—7 in FIG. 5.

Ampul 2 has its tube 4 contained within a sleeve member 50 to which a bushing 52 is secured by a pressed fit. Sleeve member 50 has a peripheral flange 54 which is held against cylinder 44 by a screw cap member 56 threadably secured to cylinder 44 at 58. Cap 56 has a front opening 60 (FIG. 6) which is partially blocked by three ears 62 which are adapted to interlock with ears 30 of ampul 2 which register with the larger radius portions of opening 60 for entry within cap 56 and then are turned clockwise as viewed in FIG. 6 for locking behind ears 62. Cap 56 has stop portions 64 which limit the rotation of ears 30. An O-ring 66 is retained by cap 56 and is abutted by the rear face of ears 30.

Figure 8:
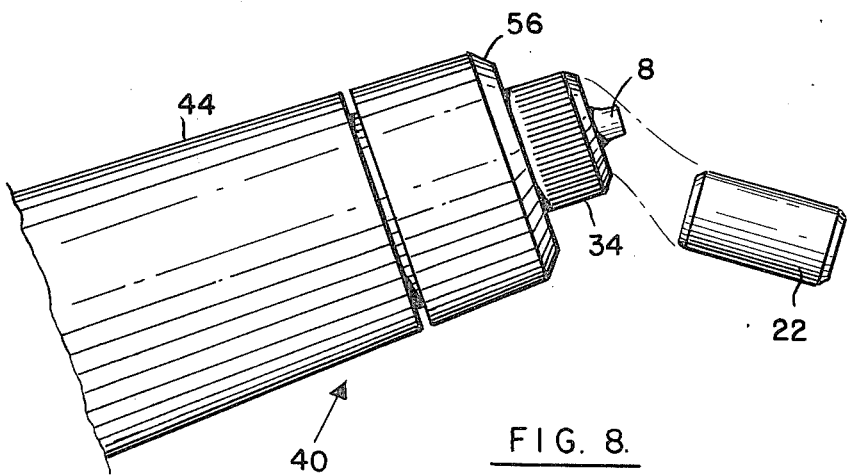
FIG. 8 is a side elevation, partially broken away, of the device of FIG. 4 showing the ampul cap removed and the ampul ready for the injection.

To carry out an inoculation, the ampul 2 is inserted into injector 40 and spool portion 34 is rotated to lock ears 30 behind ears 62. Tip 22 is then broken off exposing nozzle 8 as shown in FIG. 8. Actuating lever 42 is then depressed to cause gas to be delivered to piston 46 which in turn advances rod 49 pushing plunger 14 towards nozzle 8 and expelling the contained liquid 16. Spool portion 34 prevents the parts of injector 40 from becoming contaminated by being in contact with the skin. After the inoculation is carried out spool portion 34 is rotated counterclockwise as viewed from the front of injector 40 until ears 30 can be withdrawn from behind ears 62 and then the ampul 2 is withdrawn and disposed of.

I claim:

1. In a unit dose ampul containing medicament for a jet injector comprising a tube open at one end and having an integral nozzle at the other end and a piston in the tube to seal the open end of the tube and adapted to advance liquid in the tube through the nozzle, the improvement comprising:

a sealing cap encompassing the nozzle and said other end of the tube and secured to the tube, the cap having a peripheral area of weakness encircling the nozzle whereby a portion of the cap can be broken off to expose the discharge end of the nozzle, and means integral with the cap for removably securing the tube to a jet injector.

2. An ampul in accordance with claim 1 in which the cap has an enlarged portion between the securing means and the area of weakness to space the injector away from a patient's skin.

3. An ampul in accordance with claim 1 in which the securing means is a male portion of a bayonet joint adapted to cooperate with a female portion of a bayonet joint on a jet injector.

* * * * *